United States Patent [19]
Zurawski, Jr.

[11] 4,192,917
[45] Mar. 11, 1980

[54] PROCESS FOR ROSETTING HUMAN B LYMPHOCYTES WITH RHESUS MONKEY ERYTHROCYTE

[75] Inventor: Vincent R. Zurawski, Jr., North Reading, Mass.

[73] Assignee: Massachusetts General Hospital, Boston, Mass.

[21] Appl. No.: 27,307

[22] Filed: Apr. 5, 1979

[51] Int. Cl.$^2$ .................... C12N 7/04; A61K 39/00
[52] U.S. Cl. ................................. 435/236; 424/12
[58] Field of Search ..................... 195/1.8; 424/12

[56] References Cited
PUBLICATIONS

Barrett–Textbook of Immunology 2nd edit. (1974), p. 54.

Primary Examiner—Sam Rosen
Attorney, Agent, or Firm—Thompson, Birch, Gauthier & Samuels

[57] ABSTRACT

Human peripheral blood lymphocytes are stimulated with either a polyclonal activator or an antigen which gives rise to immunologically activated B lymphocytes. These activated B lymphocytes are separated from non-activated B lymphocytes by relying on the fact that activated B lymphocytes possess a surface marker; the ability to rosette Rhesus monkey lymphocytes (RhMRBC), not found on their non-activated counterparts. Separation is achieved by rosetting with RhMRBC and subsequent density centrifugation of cells.

11 Claims, 6 Drawing Figures

PROCESS FOR ROSETTING HUMAN B LYMPHOCYTES WITH RHESUS MONKEY ERYTHROCYTE

BACKGROUND OF THE INVENTION

The invention described herein was made in the course of work funded by U.S. Public Health Service Grants HL-19259 and CA 10126.

This invention relates to a process for separating immunologically activated human B lymphocytes from non-activated lymphocytes. Identification of surface markers and functional differences among lymphocytes obtained from various species has led to classification schems defining T and B lymphocytes and related cell types. Various subpopulations of these lymphocytes have also been identified. Functional differences among these cells and their subclasses have been recognized which reflect proliferative and differentiative states of maturation both dependent and independent of extrinsic immunological stimulation.

Populations of human T lymphocytes have frequently been defined by their ability to form rosettes with sheep erythrocytes (SRBC) although no functional evidence exists that demonstrates unequivocally that all SRBC rosetting lymphocytes are T cells or that all T cells necessarily will form SRBC rosettes. It has been suggested that human T lymphocytes might alternatively be defined by formation of rosettes with rhesus monkey erythrocytes (RhMRBC). It has been reported that human T lymphocytes, but not B lymphocytes, granulocytes or monocytes rosetted RhMRBC.

It is known that subsequent to exposure of specifically reactive B cells to antigen (in an immune response, in vivo or in vitro), such exposed cells differentiate and proliferate going on to form plasma cells which syntheize and secrete large amounts of specific antibodies. In similar fashion, several polyclonal activators (e.g., Epstein-Barr virus, Pokeweed mitogen) induce differentiation and proliferation in several clones of B cells. This polyclonal response leads to cells secreting many immunoglobulin types with multiple, usually unclassified specificities.

Production of specific antibodies in vitro in long-term continuous cell cultures requires that a set of human B cells, activated by some immunological means as described above, be converted to a long-term growing (continuously proliferating) cell line as a first step. The process of converting these cells to continuously growing cell line using Epstein-Barr virus, has been described in copending U.S. patent application Ser. No. 868,604, filed Jan. 11, 1979. Any such conversion is a multi-clonal process. Therefore, preselection of specifically (by antigen) stimulated cells provide a means to greatly enhance the chances of establishing a human B cell line with desired specificity, i.e., producing antibody to the antigen used to stimulate the B cells initially. Consequently, the utility of the invention described herein is that it enables one to separate such antigen activated human B cells prior to virus transformation, or some other technique used to convert B cells to continuous cell lines, thus greatly increasing statistical chances of obtaining cell lines synthesizing antibody specific for the activated antigen.

SUMMARY OF THE INVENTION

In accordance with this invention, immunologically activated human B lymphocytes have been separated from non-activated B lymphocytes. This invention provides a general procedure for separating activated B cells from non-activated B cells and is based upon the discovery that B cells activated with an antigen or a polyclonal activator induce the formation of a new surface marker on the activated cells. The isolation of activated cells is accomplished by rosetting human B and null cells with RhMRBC and followed with density centrifugation on a Ficoll-Hypaque gradient. Two populations of B and null cells are obtained, one clearly containing activated cells which are the most dense while the other population which is less dense comprises non-activated null cells.

DESCRIPTION OF FIGURES

The FIGURES show the results of the experiment set forth in Example I.

Panel A: donor, SW. Panel B: donor, DD. Panel C: donor, SG. Panel D: donor, ER.

Figure 6:
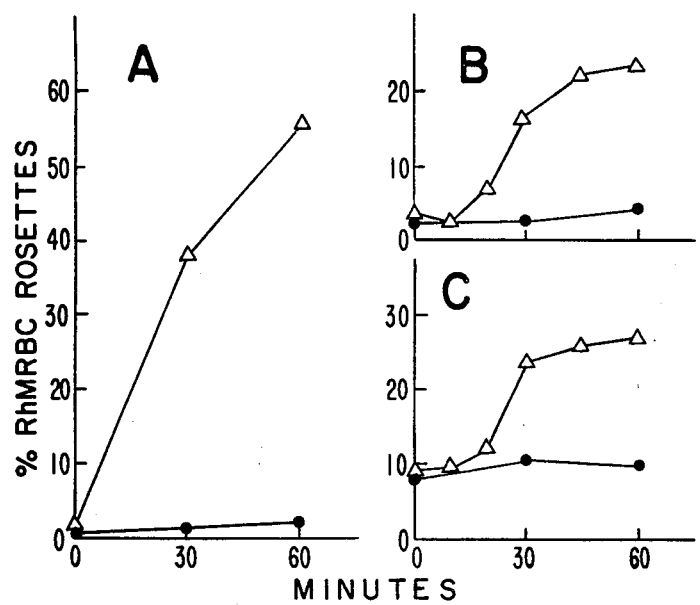

FIG. 6. In vitro induction of RhMRBC rosetting in a purified B+null cell fraction. Percent RhMRBC rosette forming lymphocytes versus minutes of incubation. ●—●, RhMRBC rosettes with no added reagent; △---△, RhMRBC rosettes with designated anti-Ig preparation. No increase in SRBC rosetting was observed. Panel A: rabbit antihuman F(ab')$_2$ antibody (20 µg per ml). Panel B: F(ab')$_2$ fragments of rabbit antihuman F(ab')$_2$ antibody (20 µg per ml). Panel C: F(ab')$_2$ fragments of rabbit anti-human F(ab')$_2$ antibody (100 µg per ml).

DESCRIPTION OF SPECIFIC EMBODIMENTS

In the process of this invention, animal lymphocyte cells are stimulated in vivo or in vitro by a polyclonal actibator, an antigen or T cell products induced by an antigen or a polyclonal activator which products normally induce B-cells to produce antibody. The animal lymphocyte cells are isolated by any conventional means such as by taking a blood sample, dilute it with a cell culture medium, centrifuge on a density gradient to isolate mononuclear cells followed by separation of monocytes to thereby recover a cell population comprising B-cells, T-cells and null cells. Stimulation of the lymphocyte cells can be effected either in the presence of or in the absence of T-cells. It it is desired to remove T-cells prior to stimulation, they are rosetted with RhMRBC followed by separation by centrifugation to obtain a cell population rich in unstimulated B-cells. The population of B-cells can then be stimulated by being allowed to incubate for a period of time to effect formation of a new surface marker on the activated cells, e.g., for three to seven days depending on the system utilized. At the end of this incubation, the population contains some activated B cells, which express a new surface marker not previously known. By the term "activated B cell" as used herein is meant B-cells with this new surface marker. The marker has the ability to rosette Rhesus monkey erythrocytes. That is, the activated cells have the property of binding to Rhesus monkey erythrocytes while the cells which remain inactive, i.e., lack the new marker, do not have the ability to rosett Rhesus monkey erythrocytes.

Subsequent to induction of the receptor, the activated non-T lymphocytes, including B lymphocytes are separated from the non-activated population. The cell population containing activated non-T cells and non-activated cells are admixed with Rhesus monkey erythrocytes under the following general conditions: A cell suspension is formed comprising an aqueous cell culture medium, e.g., RPMI-1640 which then is admixed with an aqueous cell culture medium containing RhMRBC that contains fetal calf serum. This effects rosetting (binding) of the erythrocytes specifically to only the activated cells thereby causing a selective increase in density of the activated cells. The rosetted activated cells then are separated from the less dense non-activated cells by any technique which effects separation on the basis of differential density, e.g., centrifugation on a standard Ficoll-Hypaque gradient. Alternatively, separation of activated cells may be affected by forming a layer of RhMRBC bound to a layer of poly-lysine on a support and then contacting the cell population containing activated B-cells to the RhMRBC followed by washing. The centrifugation procedure causes RhMRBC rosetting cells to be pelleted in a centrifuged tube while non-rosetting cells layer on the top of the Ficoll-Hypaque cushion. After a short time, 3 to 7 days, the rosetting fraction contain a marker for large cells in the 15-20 micron diameter range, several of which are clumped together. These cells are typical of blast cells produced by mitogen stimulation. The non-rosetting fraction contains only small lymphocytes (8-12 micron diameter). The fraction of blast cells in the rosetting fraction is found to increase generally over a 4 day period following separation. No blast cells are detected in the non-rosetting fraction after this time.

The rosetted active cells are treated to detach the RhMRBC from the active cells without destroying the active cells. This is accomplished by lysis of the RhMRBC, e.g., with water or aqueous ammonium chloride. Lymphocytes remaining are then washed and resuspended.

When lymphocytes are stimulated by specific antigen only, those B cells initially possessing surface immuno globulin receptors to that antigen will be activated. Hence, separation of antigenically specific B lymphocytes from those not activated by RhMRBC rosetting and Ficoll-Hypaque density centrifugation is achieved. For example, by in vivo boosting with an antigen, e.g., tetanus toxoid followed by isolation of lymphocytes, 7 days post-boost in general will yield cell populations without measurable increases in activated B cells, as judged by SRBC and RhMRBC analytical rosetting. These cells are separated first by RhMRBC rosetting and centrifugation to obtain a rosetting population containing T-lymphocytes and toxoid specific activated B lymphocytes. By re-rosetting these cells with SRBC and centrifuging, T-cells are removed leaving only activated B cells. Examination of these cells show a high percentage of large cells, presumably blasts, such as detected with a polyclonal activator such as pokeweed are mitogen stimulated RhMRBC rosetting fraction. Successful EBV transformation of these cells leads to cell lines capable of producing antibody to tetanus toxoid continuously.

The following example illustrates the present invention and is not intended to limit the same.

EXAMPLE I

This example illustrates that activated lymphocyte B cells rosette with RhMRBC.

Several lots of freshly isolated guinea pig erythrocytes (GPRBC) and RhMRBC (from four different monkeys) were obtained from Microbiological Associates, Walkersville, MD. Cell line NC37 was originally derived from the peripheral blood of a normal individual. It has various B lymphocyte characteristics: human B lymphoctye specific surface antigen, complement receptors, surface Ig (sIg), and Epstein-Barr nuclear antigen (EBNA). Line CEM was derived from the blood of a child with acute lymphobastic leukemia; it has various T cell characteristics, including human T lymphocyte specific antigen and the ability to rosette sheet erythrocytes (SRBC), at least at early passage. The early passage CEM human cell line is designated CEM(III). CEM is also negative for B cell markers (sgI, complement receptors, Epstein-Barr virus nuclear antigen, EBNA). Human cell line LAZ 221 was established from the peripheral blood of a patient with acute lymphocytic leukemia. It is negative for B cell and T cell markers and has been described as a "null" cell line. The term "null" cell as used herein denotes that peripheral blood lymphocyte separation which possesses neither SRBC nor sIg receptors. Human cell line K562 originally obtained from the pleural fluid of a patient with chronic myelogeneous leukemia, has the Philadelphia chromosome marker characteristic of myelogeneous leukemia cells and is negative for B cell markers (surface Ig and EBNA). Human cell line HL60 was established from peripheral blood of an adult with acute promyelocytic leukemia. The majority of these cells appear as myeloblasts and promyelocytes when stained; this line is negative for conventional T or B lymphocyte markers. Human cell line MCUV was established from B95-8 strain EBV, Epstein-Barr virus, transformation of marmoset leukocytes. Cell lines 1NBS-B1, 1NBS-C2, 1DC-5, and 4LP-C3 were produced by infection of normal human spleen cells (1NBS-B1 and C2) or human peripheral blood lymphocytes (DC-B5 and 4LP-C3) with B95-8 virus. These lines were found to contain the B cell marker, EBNA.

All cell lines were found not to contain mycoplasma by two tests: growth on agar and staining with 4'-6-diamidino-2-phenylindole obtained in kit form from Bioassay Systems, Cambridge, MA.

EB virus pools were freshly prepared from filtered cell supernatant fluids at 8-10 days after subculture of MCUV cells in RMP1 1640+10% human AB+ serum (treated as described under cell culture). Such pools contained approximately $10^5$ transformation doses per ml of EBV as determined by virus titration on human cord blood lymphocytes. Inactive EBV, Epstein-Barr virus pools irradiated by 50,000 erg per $mm^2$ ultraviolet light, (UV-EBV), was prepared by same day irradiation of virus pools with ultraviolet (UV) light in a specially designed apparatus (equipped with five Sylvania G8T5 mercury germicidal lamps). Total dose to virus pools of incident UV light at 254 nm was 50,000 ergs per $mm^2$. CEM supernatant fluids for induction experiments were prepared in identical fashion as virus pools.

Pokeweed mitogen (PWM) and lipopolysaccharide (LPS) (*E. coli*, 0127:138), the polyclonalactivators, were obtained from Grand Island Biological Co; Grand Island, N.Y. or Sigma Chemical Co; St. Louis, MO. and used without further purification. Concanavalin A (Con A) was purchased from Sigma and partially purified by $NH_4HCO_3$ precipitation. Human γ-globulin (HGG) was obtained from Miles Laboratories, Inc. or recovered from pooled human sera by 33% $(NH_4)_2SO_4$ precipitation and was further purified by ion exchange chromatography at pH 7.5 on DEAE cellulose. Cleavage of HGG with 1% Pepsin (Worthington Biochemicals, Freehold, N.J.) to obtain F(ab')$_2$ fragments was accomplished with 20 hr incubations at 37° C., pH 4.50. F(ab')$_2$ fragments were purified by G100 sephadex chromatography, followed by Protein A Sepharose (Pharmacis, Piscataway, N.J.) chromatography in Tris buffer (0.01 M Tris-HCl, 0.15 M NaCl, pH 7.80).

Fluorescein labeled polyvalent antibody directed against human lgA, lgG and lgM (heavy chain specific) was purchased from Behring Diagnostics. Polyvalent (anti-lgA, lgG, lgM0 immunoadsorbent beads were obtained from BioRad Laboratories, Richmond, CA. Antibodies to human F(ab')$_2$ were obtained from the sera of rabbits immunized, and boosted after four months, with F(ab')$_2$ fragments (1 mg) in complete Freund's adjuvant via toepad and intradermal routes. These antibodies were purified by immunoadsorbent chromatography on human F(ab')$_2$ Sepharose 4B columns using 1 M acetic acid to elute bound anti-F(ab')$_2$ antibodies. Active F(ab')$_2$ fragments of these antibodies were produced as above by pepsin digention except that incubations were for 4 hr instead of 20 hr. Purification of these fragments was done as above.

Na $^{125}$I and [$^3$H] thymidine were purchased from Amersham Searle, Chicago and New England Nuclear, Boston, respectively. Iodination of antibody was performed using 1 mCi $^{125}$I per μg of protein as described in Biochem. J., 113:299.

Continuous cell lines were maintained as stationary suspension cultures in RPM1 1640 medium (Grand Island Biological) supplemented with 10% γ-irradiated fetal calf serum (FCS) (Microbiological Associates), 2 mM glutamine, penicillin and streptomycin, in a humid atmosphere of 5% $CO_2$ in air at 37° C. Donor lymphocytes which were cultured for experimental purposes were maintained in RMP1 1640 supplemented with 10% human AB+ serum, penicillin and streptomycin and additional additives at a cell density of $2 \times 10^6$ ml. The human AB+ serum was obtained from a single male donor. It was HGG depleted by 33% $(NH_4)_2SO_4$ precipitation followed by dialysis against 0.01 M phosphate, 0.15 M NaCl, pH 7.4 (PBS). It was then heat inactivated at 56° C. for 2 hr and filtered through a 0.45 μm filter before use.

A portion of cell line MCUV was maintained in medium containing this AB+ serum to provide virus free of FCS. A portion of cell line CEM was also maintained in this medium, to provide a human lymphoblastoid cell line supernatant fluid free of FCS.

Preparation of Donor Lymphocytes

Blood samples were collected in heparinized vessels, diluted 1:1 with RMP1 1640 cell culture medium and fractionated by bouyant density centrifugation on Ficoll-Hypaque, (Scand. J. Clin. Lab. Invest., 21, Suppl. 97:77). Recovered monoculear cell suspensions were thoroughly washed at least three times with excess RMP1 1640, then monocyte depleted by adherence to plastic dishes for 1-2 hr to yield peripheral blood lymphocyte (PBL) preparations.

Separation of B and T Lymphocytes

Three techniques were used to separate B and T lymphocytes: SRBC or RhMRBC rosetting followed by Ficoll-Hypaque density centrifugation, fractionation on nylon wool columns, or fractionation on Sepharose 6B to which rabbit antihuman F(ab')$_2$ antibodies were attached by CNBr treatment.

For rosetting, PBL suspensions at a density of $30 \times 10^6$ cells per tube in RPM1 1640 were placed in 50 ml round bottom Oak Ridge type centrifuge tubes obtained from Scientific Products. Two ml of a 5% v/v solution of SRBC (or RhMRBC), in PBS containing 10% heat inactivated and SRBC (or RhMRBC) adsorbed FCS, were then added. The tubes were incubated at 37° C. for 10 minutes and centrifuged at $200 \times g$ for 5 min. After a 1 hr incubation at 25° C., the rosettes were gently resuspended by tapping. The suspensions were then underlayered with 5 ml of Ficoll-Hypaque and centrifuged for 20 min at $1200 \times g$. The nonrosetting (B+null cell) fractions were collected and washed twice with RPM1 1640. The rosetted (T cell) fractions were treated with 1 ml sterile twice distilled $H_2O$ for 15 sec to lyse the erythrocytes. They were then immediately washed twice with a 50-fold excess of RPM1 1640 and collected. The entire procedure was repeated for each batch of cells to obtain purified T cells and B+null cell fractions.

Nylon wool columns were prepared as follows: Barrels of 12 ml plastic syringes fitted with sterile disposable stopcocks (Pharmascal Laboratories, Glendale, CA) were packed with nylon wool to the 6 ml mark, sterilized and washed before use with 50 ml RPM1 1640 medium at 37° C. The columns were sealed with parafilm and incubated upright at 37° D. for 30 min. Three ml of a $20 \times 10^6$ per ml PBL suspension in RPM1 containing 10% FCS was added dropwise to the columns which were then sealed and incubated for one hour at 37° C. Effluent cells were collected by washing the column with 25 ml RPMl containing 10% FCS added dropwise followed by an additional 100 ml added rapidly. Nylon adherent cells were eluted next by adding 5 ml RPMl containing 10% FCS to the column, squeezing and pressing the nylon wool with sterile forceps, draining the column and repeating the process five times. The two cell populations were then centrifuged separately and resuspended at $2 \times 10^6$ cells per ml for further use.

Sepharose 6B-rabbit antihuman F(ab')$_2$ columns were prepared by activating 30 ml Sepharose 6B with 200 mg CNBr (51,52) at pH 10.5. The activated material was then washed with 200 ml borate buffer (0.01 M Na$_2$B$_2$O$_7$, 0.15 M NaCl, pH 8.3) and added to 25–30 mg of purified antibody in borate buffer. The coupled Sepharose was then stirred slowly overmight at 4° C. and stored in PBS with 0.02% NaN$_3$. B cell and T+null cell fractions were collected from these columns as described in J. Immunol., 113:1113.

Analytical Erythrocyte Rosetting

Rosetting of SRBC, RhMRBC and GPRBC were all done as follows: 0.4 ml of 1% erythrocytes in PBS containing 10% heat inactivated FCS absorbed with appropriate erythrocytes was mixed with an equal volume of lymphocyte suspension in RPM1 1640 containing 25% absorbed, inactivated FCS at $2 \times 10^6$ cells per ml. A brief incubation of 37° C. (5–10 min) preceded a 5 min centrifugation at 200×g followed by a 3 hr incubation of the pellet at 4° C. We observed no significant difference in the numbers of RhMRBC rosette forming cells with 3 hr, 4° C. incubations as compared to 60 min, 25° C. incubations. Omission of the 37° C. incubation step did not significantly alter these results. Use of absorbed, inactivated human AB+ serum in place of FCS did not significantly alter the results. Lymphocytes or red cells were not treated with any rosette stabilizing agents. Gently resuspended cells were carefully aspirated in a pasteur pipette with a widened bore and placed in a hemocytometer chamber for enumeration of rosette forming cells; three or more erythrocytes adherent to a lymphocyte classified it as a rosette forming cell. A minimum of 200 lymphocytes was always counted. Trypan blue was routinely added to lymphocyte preparations to assess cell viability. In most experiments crystal violet was added to Rh-MRBC rosette suspensions to help visualize lymphocytes.

Identification of Lymphocytes with Surface Ig (sIg)

Polyvalent anti-IgA, -IgC, IgM antibody coupled to fluorescein isothiocyanate was used to visualize surface Ig. Cells were incubated for 20 min in Hanks balanced salt solution at 37° C. prior to examination. Fixed cells were counterstained with Evans blue to better visualize nonreacting cells. Alternatively, polyvalent immunoadsorbent beads were also used to ascertain quantitatively sIg bearing lymphocytes.

Induction Experiments

In vitro experiments to detect the ability of certain reagents to induce RhMRBC rosetting cells were conducted with PBL from healthy adult donors. Macrophage depleted mononuclear cell suspensions at $2 \times 10^6$ cells per ml in RPMl 1640 supplemented with 10% AB+ serum (treated as described under cell culture) and additional additives (Cellular Immunol., 3:264) were plated in Costar 24 well tissue culture plates at 1 ml per well.

FCS (Grand Island Biological Lot C381021, 100 $\mu$l) or PWM, Con A or LPS at a concentration of 5 $\mu$g per ml were added to cells in culture plates. The cells were allowed to incubate at 37° C. and were removed at several intervals over the course of a week and assayed for RhMRBC and SRBC rosetting capability using the methods described above. To examine the ability of EBV to induce RhMRBC forming cells in PBL populations, two approaches were used to expose cells to virus. PBL were suspended in EBV or UV-EBV at $1 \times 10^7$ cells per ml for 2 hr at 37° C. with gentle shaking, then washed twice with a large excess of medium and placed in culture plates as described above. This was termed method A. Alternatively, 100 $\mu$l aliquots of EBV or UV-EBV were added to cells already in culture plates. This was termed method B. Rosetting capability was measured at several intervals as in mitogen induction experiments. Supernatant fluids from cell line CEM were collected after 8–10 days and tested for induction capability via method B. CEM supernatant fluids irradiated with UV light as described above were also tested.

Simultaneously, synthesis of DNA was monitored by [$^3$H] thymidine uptake. Briefly, cells were treated as above but plated in 96 well Costar tissue culture plates at 0.1 ml per well. Twenty-five $\mu$l of a 100 $\mu$Ci per ml preparation of [$^3$H] thymidine in RPMl 1640 was added to wells to be assayed and the cells were allowed to incubate for 4 hr. Cells were then harvested with a CHAP-100 cell harvester obtained from ADAPS, Inc., Dedham, MA. After drying, filter disks with harvested cells were placed in scintillation vials containing 10 ml Omnifluor (New England Nuclear, Boston, MA). Vials were then counted using a Packard Model 2450 liquid scintillation spectrometer.

Anti-Ig induction of RhMRBC rosetting was performed as follows: cell suspensions at 0° C. and $2 \times 10^6$ cells per ml RPMl 1640 in 12×75 mm Pyrex test tubes were treated with 20 $\mu$g or 100 $\mu$g per ml of column purified rabbit antihuman F(ab')$_2$ or F(ab')$_2$ fragments of this antibody. The suspensions were maintained at 0° C. for 30 min, washed twice with excess medium at 0° C. and placed in a 37° C. water bath. Samples were taken at 5–10 min intervals for 1–2 hr and assayed for RhMRBC rosetting ability.

Results

Cells Lines

Several established human cell lines were tested for their ability to form rosettes with RhMRBC, SRBC and as a negative control, GPRBC. A large fraction of cells from each of these lines was found to rosette RhMRBC despite the varied phenotypic characteristics of the lines (Table I). Except for CEM and CEM (111), none of the lines were derived from a T cell malignancy; therefore, they did not possess conventional T cell markers. Consequently, cell lines NC37, K562, HL60 and LAZ221 did not form SRBC rosettes. None of the lines rosetted GPRBC.

All of the human cell lines established from lymphocytes infected in vitro with EBV also formed RhMRBC rosettes. This was the case regardless of whether cells were derived from splenic or peripheral blood lymphocytes. Representative examples are shown in Table I.

These data suggest that leukocytes other than T lymphocytes also possess a receptor responsible for RhMRBC rosetting. In particular, non-T lymphocytes are implicated as potential rosette formers with RhMRBC. To examine this possibility, lymphocytes from several donors were tested for their ability to form RhMRBC rosettes.

Peripheral Blood-Lymphocytes of Normal Donors and Patients with Hematologic Disorders Lohrmann and Novikovs, (Clin. Immunol. Immunopath., 3:99), presented rosetting data from four individuals that suggested the RhMRBC rosetting capability was associated only with hyman T-lymphocytes of normal individuals. Table II presents percentages of RhMRBC and SRBC rosetting lymphocytes obtained from the peripheral blood of 23 donors. Rosetting of GPRBC was not observed in any case. For 19 individuals, the fraction of lymphocytes forming rosettes with RhMRBC and SRBC was virtually identical. However, in one case, donor GC, fewer RhMRBC rosette forming cells were present than cells that formed SRBC rosettes. Conversely, in three cases, donors SS, JB and LP, a greater number of cells that rosette RhMRBC were present in the PBL population than those that formed SRBC rosettes. RhMRBC are visibly larger than SRBC. Therefore, careful examination of cells forming rosettes in the presence of both types of erythrocytes could distinguish the kinds of erythrocyte rosetting with each cell. A population of lymphocytes that formed rosettes only with RhMRBC and not with SRBC was clearly distinguished visually with lymphocytes from donors SS, JB and LP. The existence of this RhMRBC rosetting population was found to be a transient phenomenon in at least two individuals. Six and 20 weeks respectively, subsequent to the initial rosetting study, the fractions of SRBC and RhMRBC rosetting lymphocytes obtained from donors LP and SS coincided. Consequently, while it may be generally true that RhMRBC rosetting detects the same population of human PBL as SRBC rosetting, it is not uncommon to find putatively normal donors whose lymphocytes do not rosette RhMRBC and SRBC in equal numbers.

We also investigated the RhMRBC and SRBC rosetting propensities of lymphocytes obtained from a small number of individuals with hematologic disorders. Two patients with acute mononucleosis (RS and MJ) exhibited no discrepancy between RhMRBC and SRBC rosetting lymphocytes (Table III) despite differential blood counts (data not shown) typical of mononucleosis. Therefore, in these two cases, at least, the virocytemia which can be associated with mononucleosis was evidently not sufficient to induce any alteration in the usual balance between RhMRBC and SRBC rosetting PBL. Lymphocytes from two of three patients with leukemia showed a greater fraction of cells forming RhMRBC rosettes than SRBC rosettes (Table III).. The difference was especially marked in patient LM, with chronic lymphocytic leukemia; this is in accord with data of Lohrmann and Novikovs. Lymphocytes from an acute lymphocytic leukemia patient (VC) in partial remission after chemotherapy showed an excess of RhMRBC over SRBC rosetting cells. In contrast, lymphocytes from patient AM, with a lymphosarcoma cell leukemia and who had been refractory to chemotherapy, did not exhibit an excess of RhMRBC over SRBC rosetting cells. A significant decrease below normal levels (Table III) was seen in the number of lymphocytes forming both RhMRBC and SRBC rosettes from patient AM, however. Hence, with PBL obtained from patients with hematologic malignancies, alterations in the ratio of cells which form rosettes with SRBC and RhMRBC can sometimes be expected.

Induction of RhMRBC Forming Cells in Vitro

The ability to rosette RhMRBC was demonstrated for non-T lymphocytes (i.e., non-SRBC rosetting cells) of normal donors, for several cell lines of varied origin, and PBL presumably of leukemic origin. Further, this phenomenon could be transient in normal individuals. We, therefore, decided to investigate whether this capability might be induced in non-T lymphocytes from normal donors.

Figure 1:
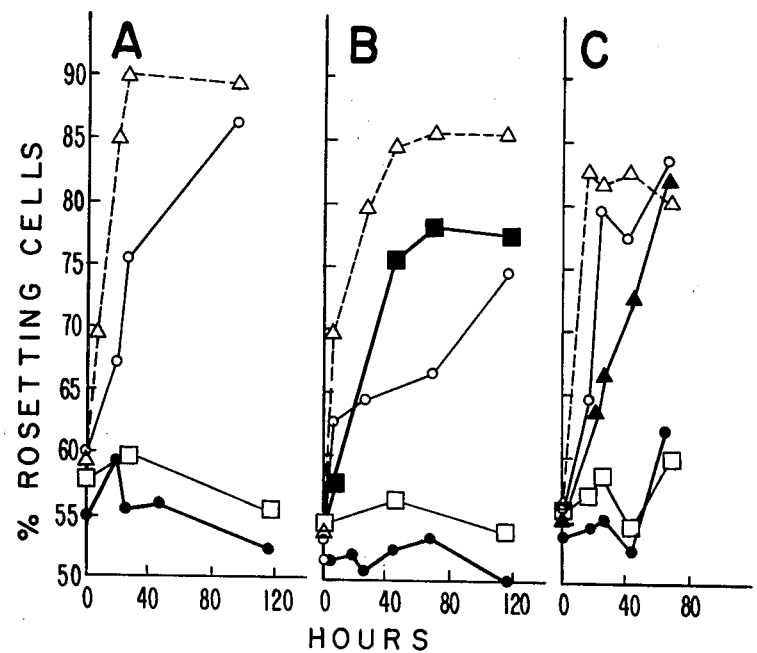
FIG. 1. In vitro induction of RhMRBC rosetting in PBL by mitogen stimulation. Percent SRBC or RhMRBC rosette forming lymphocytes versus hours of incubation. ● — ●, RhMRBC rosettes with no added reagents; □—□, SRBC rosettes with 5 µg per ml PWM, Con A and LPS or with 100 µl FCS (average of controls for each donor); ∆- - -∆, RhMRBC rosettes with 5 µg per ml PWM; ■ — ■, RhMRBC rosettes with 5 µg per ml Con A; ▲—▲, RhMRBC rosettes with 5 µg per ml LPS; o — o, RhMRBC rosettes with 100 µl FCS (Grand Island Biological Lot C381021). Panel A: donor, PE. Panel B: donor, MC. Panel C: donor, BC.

Lymphocytes were isolated from healthy adult donors and placed in culture. It was noted that FCS (Lot C381021) could induce excess RhMRBC rosetting cells in vitro (FIG. 1). Hence, assays were carried out in medium supplemented with 10% human AB+ serum obtained from an individual male donor. This serum was heat inactivated and depleted of HGG as described above. FIG. 1 illustrates the induction of excess RhMRBC rosetting cells in vitro in the presence of various reagents. LPS, PWM or Con A each cause an increase in the fraction of lymphocytes rosetting RhMRBC, whereas SRBC rosetting cells remained at initial values. Up to 93% of the lymphocyte population was found to rosette RhMRBC after in vitro culture with these substances. The percent of lymphocytes in control cultures rosetting RhMRBC and SRBC remained the same (55–65%).

Figure 3:
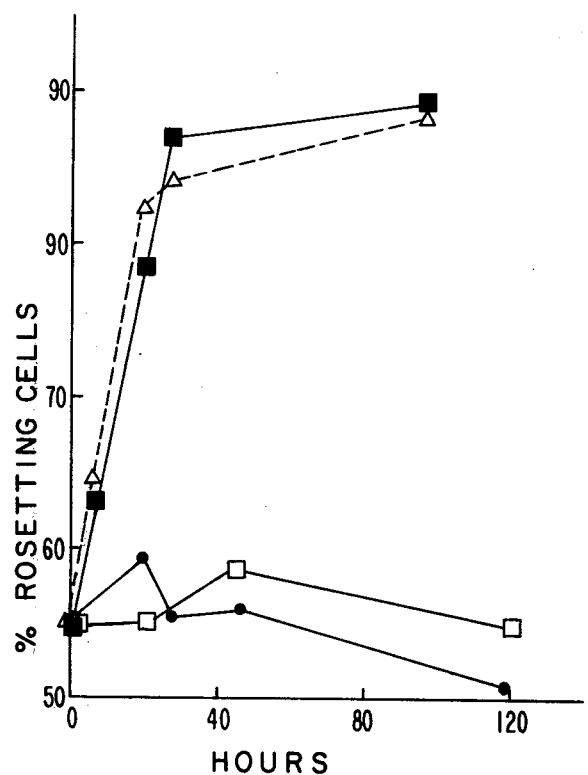
FIG. 3. In vitro induction of RhMRBC rosetting in PBL of donor PE by CEM supernatant fluids. Percent SRBC or RhMRBC rosette forming lymphocytes versus hours of incubation. ● — ●, RhMRBC rosettes with no added reagents; □—□, SRBC rosettes with 100 µl CEM conditioned medium; ∆- - -∆, RhMRBC rosettes with 100 µl CEM conditioned medium; ■ —■, RhMRBC rosettes with 100 µl of UV-treated (50,000 ergs per cm$^2$) CEM conditioned medium.

To determine whether or not a secreted or shed product of another lymphoblastoid line besides MCUV might serve to induce an increase in the fraction of lymphocytes rosetting RhMRBC, cell supernatant fluids from cultures of the human cell line CEM were also examined. FIG. 3 illustrates the induction of RhMRBC rosetting by a CEM culture fluid. UV inactivated CEM supernatant fluids were just as efficient at this induction suggesting that live virus was not responsible for the induction as is very likely with MCUV supernatant fluids (EBV). Again, no increase in SRBC rosetting was noticed with either CEM supernatant preparation. Thus, a product other than a live virus, of a human lymphoblastoid line, in this case of T cell origin, can also induce RhMRBC rosetting.

Concomitant examination of [$^3$H] thymidine uptake by lymphocytes, as a measure of DNA synthesis, was accomplished in these stimulation experiments. Data for experiments using mitogenic agents is shown in Table IV. With CEM supernatant fluids and with LPS, little or no increase in [$^3$H] thynidine uptake was observed. With EBV, somewhat variable responses were noted, however, the virus did not induce much [$^3$H] thymidine uptake even after seven days (data not shown) in the experiments illustrated in FIG. 2. With PWM, stimulation indices were generally maximal in the 3–6 day range, and with Con A, they were maximal after five days of incubation and decreasing by nine days. This is in agreement with previous data regarding the kinetics of these mitogenic responses. With FCS, we observed increases in stimulation indices also, not with peaks in the 3-6 day range, however. Rather, uptake was still increasing, at least up to day nine, in one of the experiments. These data are in general contrast to RhMRBC rosetting data. With all agents except FCS (PWM, Con A, LPS, EBV, CEM supernatant fluids), maximal RhMRBC rosetting had occurred by no later than 40 hr after initiation of the experiment. Hence, expression of the increased rosetting propensity by non-T lymphocytes is not directly correlated with DNA synthesis and, by implication, not directly with a proliferative response.

These data provide substantial indirect evidence that B cells, and/or null cells, normally lacking the ability to form RhMRBC rosettes can be induced to form these rosettes by one of several stimuli. To show that B cells could form RhMRBC rosettes after stimulation, in addition EBV induction, several other experiments specifically directed at B cells were performed.

Direct evidence for induction of rosette forming capacity in B cells was obtained by treating PWM-stimulated cells with fluoresceinated polyvalent anti-Ig prior to rosetting with RhMRBC. Rosettes containing sIg positive lymphocytes were observed. Rosetting experiments were also performed with a mixture of anti-Ig immunobeads and RhMRBC. Examination of these rosettes indicated that several were composed of both beads and RhMRBC, again indicating the presence of B lymphocytes which were induced to rosette RhMRBC. These studies were difficult to quantitate, however.

Figure 4:
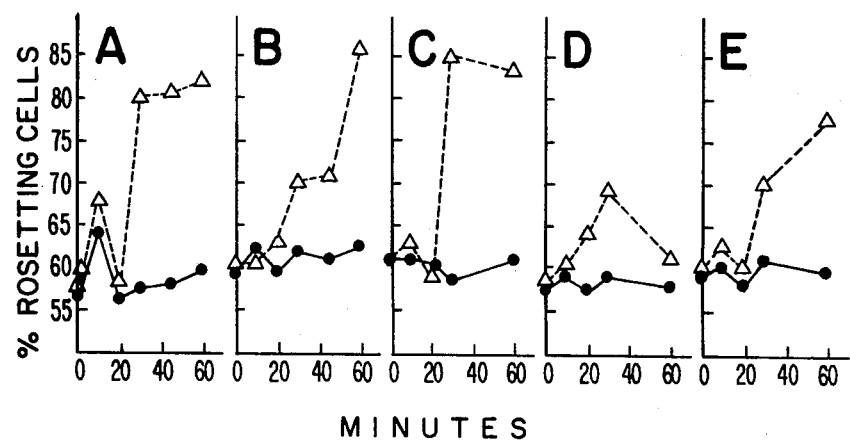
FIG. 4. In vitro induction of RhMRBC rosetting in PBL by anti-lg antibody. Percent RhMRBC rosette forming lymphocyte versus minutes of incubation. o — o, RhMRBC rosettes with no added anti-lg; ∆—∆, RhMRBC rosettes with 20 µg per ml purified rabbit antihuman F(ab')$_2$ antibody. No increase in SRBC rosetting was observed. Panels A and E: donor, AL. Panel B: donor, DD. Panel C: donor, AB. Panel D: donor, GM.
Figure 5:
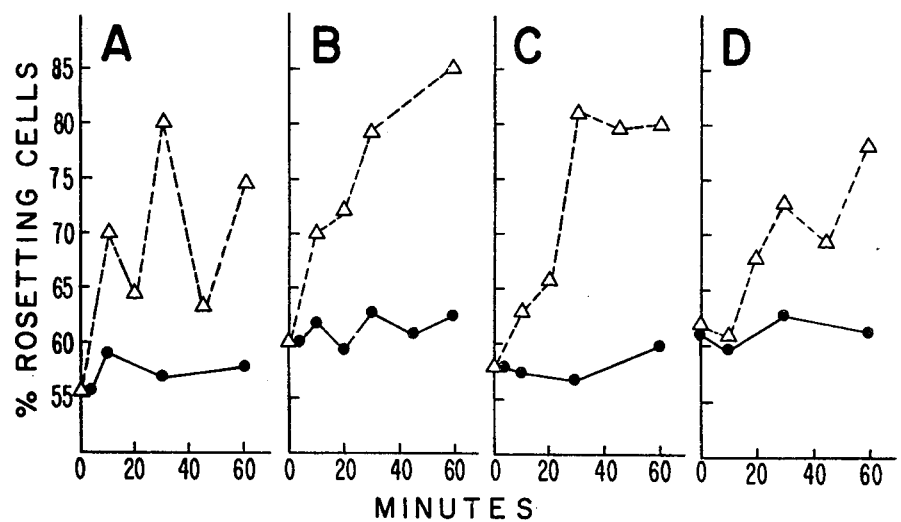
FIG. 5. In vitro induction of RhMRBC rosetting in PBL by F(ab')$_2$ fragments of anti-lg antibody. Percent RhMRBC rosette forming lymphocytes versus minutes of incubation. ● — ●, RhMRBC rosettes with no added reagent; ∆- - -∆, RhMRBC rosettes with 20 µg per ml purified F(ab')$_2$ fragments of rabbit antihuman F(ab')$_2$ antibody. No increase in SRBC rosetting was observed, nor was any increase in RhMRBC rosetting observed using 20 µg per ml of rabbit antitetanus toxoid antibody.

Antihuman F(ab')$_2$ is a specific reagent for B cells, since neither T nor null cells have sIg. Peripheral blood lymphocytes of normal donors were treated with 20 $\mu$g per ml of immunospecifically purified antihuman F(ab')$_2$ antibody and incubated for up to 90 min. A marked increase in the fraction of cells forming RhMRBC rosettes was observed (FIG. 4). This increase was not seen without anti-F(ab')$_2$ antibody nor with a purified rabbit antibody (20 ug per ml) to tetanus toxoid. No increase in SRBC rosetting cells was observed in response to anti-F(ab')$_2$. Peak number of RhMRBC rosetting cells generally appeared by 40-60 min after exposure to antibody. RhMRBC rosetting cells were also induced by exposing lymphocytes to F(ab')$_2$ fragments of the human-F(ab')$_2$ specific antibody (FIG. 5). Again, no increase in SRBC rosetting cells was observed. This induction of rosetting cells by antibody fragments suggested that sIg rather than Fc receptors played a definite role in the induction process.

To determine whether this phenomenon could occur in B cell populations separated from T lymphocytes, PBL was fractionated by four methods: chromatography on either a nylon wool column, or a Sepharose 6B column to which rabbit antihuman-F(ab')$_2$ antibody was bound, or by rosetting with either SRBC or RhMRBC followed by Ficoll-Hypaque density centrifugation. Both the cells nonadherent to the nylon wool column as well as those eluted from the anti-Ig column were markedly depleted of cells forming erythrocyte rosettes with SRBC. These principally non-T lymphocyte fractions showed substantial rosetting capacity with RhMRBC, however, suggesting that passage over either column could induce the RhMRBC rosetting phenomenon in non-T lymphocytes (Table V). Hence, they could not be used in induction experiments.

Similarly, the fraction containing B cells obtained from the SRBC rosette purification technique, also substantially depleted of T cells, often contained a large percentage of cells which formed RhMRBC rosettes (Table V). The RhMRBC rosetting and nonrosetting fractions were also separated. Table VI illustrates the results of a typical two-step purification. Lymphocytes from this donor rosetted equivalent numbers of RhMRBC and SRBC before separation. The supernatant cell fraction (nonrosetting) from an RhMRBC rosetting preparation did not form RhMRBC or SRBC rosettes (Table V and VI). Since all reagents except the red cells were identical in SRBC and RhMRBC preparative rosetting, SRBC can also cause induction of the RhMRBC rosetting capacity in non-T lymphocytes. As illustrated by data in Table V and VI, it was observed generally that fractionation of cells using the RhMRBC rosetting technique yielded a B+null cell (nonrosetting) fraction of lymphocytes containing only 1-3% of cells rosetting either SRBC or RhMRBC, and substantially increased in the fraction of cells with sIg.

Because preparative rosetting with RhMRBC resulted in a Ficoll-Hypaque interface population of cells (nonrosetting B+null cell) no longer reactive with either rhMRBc or SRBC, induction with antihuman F(ab')$_2$ antibody could be tested unequivocally. Substantial increases in RhMRBC rosetting cells were observed in this B+null cell population in response to antihuman F(ab')$_2$ as well as F(ab')$_2$ fragments of this antibody (FIG. 6). Control populations did not increase the fraction of cells rosetting RhMRBC. The fraction of SRBC rosetting cells was not altered after exposure to antibody.

It has been proposed that among human lymphocyte populations RhMRBC rosetting capacity may be a marker for T cells. I now observe that several established human cell lines of different origin form rosettes with RhMRBC (Table I). Lymphoid cell lines, classified by means of other markers as B cell derived (NC37), T cell derived (CEM), and null cell derived (LAZ221) formed RhMRBC rosettes. Also, HL60 and K562 both likely to be myeloid cell lines, formed RhMRBC rosettes. Moreover, cell lines established in our laboratory by transformation of human PBL and spleen cells with EBV all formed rosettes with RhMRBC. Since B, and not T lymphocytes, possess receptors for EBV, and since these lines (except 1NBC-C2) were shown to synthesize and elaborate Ig, these were classified as B cell derived. In contrast to these results, Lohrmann and Novikovs found that the cell line IM-9 also having B cell markers did not form RhMRBC rosettes. Although IM cells may never have had the ability to rosette RhMRBC, it is also conceivable that this line could have lost this ability after long-term in vitro culture. The demonstration that many continuously growing cells of varied origin had the ability to form RhMRBC rosettes suggested that this might not be strictly a T cell property.

Experiments with PBL of normal donors provided further evidence to this effect. The fraction of PBL from 4 of 23 donors that rosetted RhMRBC and SRBC was always identical (Table II). In three cases, more RhMRBC than SRBC rosettes were counted. The ability to form excess RhMRBC rosette was observed to be a transient phenomenon in two of these three cases over the time course of the experiments. This suggested that in isolated peripheral lymphocytes from apparently healthy individuals, non-T lymphocytes could also rosette RhMRBC.

Two mononucleosis patients in the acute phase of the illness with lymphocytosis and the presence of atypical lymphocytes did not exhibit excess RhMRBC rosetting rosetting (Table III). In contrast, the excess RhMRBC rosetting was observed in two patients with either chronic or acute lymphocytic leukemia. However, a patient (AM) with leukemic lymphosarcoma did not show an excess of RhMRBC but had a depletion of T cells as measured by SRBC and RhMRBC rosetting. Thus, some neoplastic lymphoid cells may develop the ability to bind RhMRBC but not SRBC.

In vitro induction experiments indicated that the number of lymphocytes specifically binding RhMRBC were increased by a number agents without altering the number of lymphocytes rosetting SRBC. The first agent identified which could induce RhMRBC rosetting was FCS (FIG. 1). It is uncertain what constituents of the serum were responsible for the induction, however, two substances of potential interest were considered, bacterial endotoxin, sometimes found contaminating FCS preparations, or proteins which are normal constituents of FCS, e.g. $\alpha_1$-fetoprotein. Human $\alpha_1$-fetoprotein, at least, is known to effect properties of human lymphocytes.

The mitogens PWM and ConA could induce an increase in RhMRBC rosetting (FIG. 1) without affecting the number of cells rosetting SRBC. Thus, in addition to their ability to stimulate polyclonal lymphocyte proliferation or differentiation, they also can play a role in unconvering a new surface marker in human non-T lymphocytes. Since Con A, and with human cells, perhaps PWM, are thought not to directly act on B lymphocytes, it is possible that the action of these two reagents may require T cells acting as an intermediate in the transmission of a signal leading to expression of the rosetting ability in either B or null cells. LPS, which is not substantially mitogenic to human PBL, also was capable of inducing an increase in the fraction of PBL rosetting RhMRBC. This correlated well with $^3$H thymidine uptake experiments indicating that increases in DNA synthesis need not be directly associated with the appearance of RhMRBC rosetting.

Figure 2:
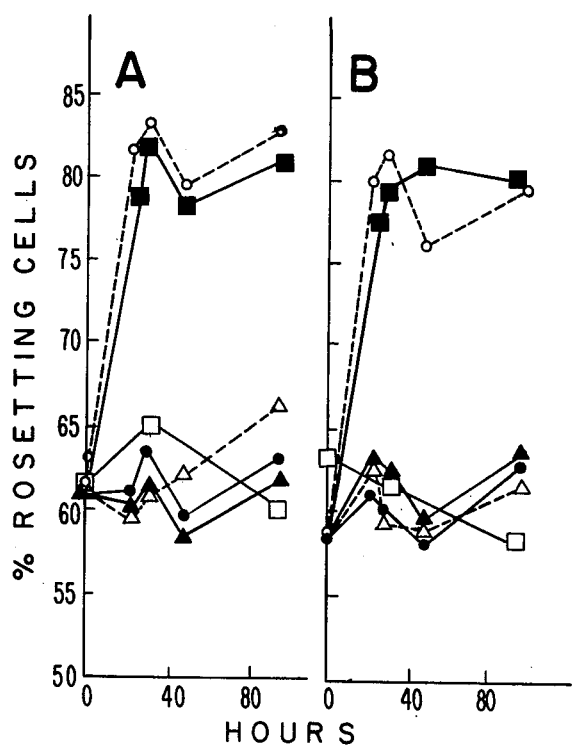
FIG. 2. In vitro induction of RhMRBC rosetting in PBL by EVB. Percent SRBC or RhMRBC rosette forming lymphocytes versus hours of incubation. ● — ●, RhMRBC rosettes with no added EBV; □—□, SRBC rosettes with added EBV (average of methods A and B); o — o, RhMRBC rosettes with method A EBV; ∆—∆, RhMRBC rosettes with method A UV-EBV; ■—■, RhMRBC rosettes with method B EBV, ▲—▲, RhMRBC rosette with method B UV-EBV. Panel A: donor, MC. Panel B: donor, PE.

Anti-F(ab')$_2$ antibody is a reagent specific for B cells. When lymphocytes were exposed either to antihuman (F(ab')$_2$ antibody or the F(ab')$_2$ fragment of this antibody, RhMRBC rosetting could be demonstrated within 30 min (FIGS. 4, 5, 6) as opposed to several hours after exposure to LPS, Con A, PWM or EBV (FIGS. 1, 2). The rapidity of this induction may be related to capping, known to occur after exposure to anti-lg, at least with murine lymphocytes, within 10 min. It is also of interest that Lohrmann and Novikovs demonstrated RhMRBC rosettes associated with non-T lymphocytes 30 min after neuaminidase treatment, suggesting that the RhMRBC binding sites may be present, but masked in these cells.

RhMRBC rosetting, which seems to occur on human B cells after mitogen exposure, after polyclonal activation by EBV, and after stimulation by anti-F(ab')$_2$ reflects the exposure of new binding sites in association with cell activation. It is a useful marker for a functional state of human B cell differentiation and it provides a tool for activated B cell isolation.

TABLE I

RhMRBC and SRBC Rosetting by Various Human Cell Lines

| Cell Line | Percent RhMRBC Rosette Forming Cells | Trials | Percent SRBC Rosette Forming Cells | Trials |
|---|---|---|---|---|
| CEM[a] | 66 | 5 | 0 | 2 |
| CEM (111)[a] | 64 | 2 | 13 | 2 |
| NC37[b] | 67 | 5 | 0 | 1 |
| K562[c] | 67 | 1 | 0 | 1 |
| HL60[d] | 94 | 1 | 0 | 1 |
| LAZ221[e] | 100 | 1 | 0 | 1 |
| 1NBS-B1[f,g] | 90 | 2 | 0 | 2 |
| 1NBS-C2[f] | 100 | 2 | 0 | 2 |
| 1DC-B5[g,h] | 85 | 1 | 0 | 1 |
| 4LP-C3[g,h] | 98 | 1 | 2 | 1 |

[a]Cell line CEM was derived from an acute lymphoblastic leukemia patient and is thought to be of T cell origin (28,29). CEM (111) represents an early passage of this line.
[b]Cell line NC37, derived from a normal donor, was found to be of B cell origin.
[c]K562 was established from a chronic myeloid leukemia patient and is thought to be a myeloid line. It is marked by the presence of the Philadelphia chromosome.
[d]HL60 is also of myeloid origin and the majority of cells from this line morphologically resemble promyelocytes and myeloblasts.
[e]LAZ221 has been classified as a null cell line; it was obtained from an acute lymphoblastic leukemia patient.
[f]Cell lines 1NBS-B1 and C2 were both established in this laboratory by in vitro infection of normal human spleen cells with EBV.
[g]These lines were found to be elaborating Ig into cell culture media.
[h]Cell lines 1DC-B5 and 4LP-C3 were established in this laboratory by in vitro infection of human PBL with EBV.

TABLE II

RhMRBC and SRBC Rosetting by Peripheral Lymphocyte of Normal Donors[a]

| Donor | Percent RhMRBC Rosetting Cells | Percent SRBC Rosetting Cells | Percent SRBC + RhMRBC Rosetting Cells[b] | Trials |
|---|---|---|---|---|
| AL | 55 | 53 | 55 | 2 |
| MC | 62 | 57 | N.D.[c] | 2 |
| GM | 59 | 58 | 63 | 7 |
| DC | 66 | 63 | 64 | 2 |
| JG | 58 | 61 | 62 | 1 |
| BK | 62 | 64 | 64 | 2 |
| ER | 62 | 63 | N.D. | 1 |
| LK | 67 | 62 | 68 | 1 |
| MB | 64 | 62 | 63 | 1 |
| AB | 62 | 63 | 64 | 2 |
| RC | 59 | 60 | 65 | 1 |
| LS | 69 | 66 | 66 | 1 |
| BR | 62 | 60 | 62 | 1 |
| SW | 63 | 62 | N.D. | 1 |
| PE | 56 | 58 | N.D. | 2 |
| BC | 56 | 58 | N.D. | 1 |
| SC | 66 | 62 | 64 | 1 |
| PB | 62 | 60 | 63 | 1 |
| ES | 64 | 60 | 62 | 1 |
| GC | 44 | 67 | 64 | 1 |
| SS[d] | 84 | 60 | 83 | 2 |
| SS[e] | 64 | 65 | N.D. | 1 |
| LP[d] | 80 | 60 | 83 | 3 |
| LP[f] | 62 | 59 | N.D. | 1 |
| JB[g] | 82 | 64 | 81 | 4 |

[a]Donors were apparently healthy adults, approximately equivalent numbers of males and females, ages 20-56, with all major ABO blood groups represented. No correlation between RhMRBC rosetting and any of these factors was noticed. Percent rosetting cells are mean values where more than one trial has been done.
[b]Equal numbers of SRBC and RhMRBC were mixed together; rosettes were generated as described in Materials and Methods to ascertain the numbers of simultaneous rosettes formed.
[c]N.D. = Not Done.
[d]Initial trials were 4.5 weeks apart.
[e]Results 20 weeks after the initial trial.
[f]Results 6 weeks after the initial trial.
[g]These four trials were conducted over a time span of 20.5 weeks.

TABLE III

RhMRBC and SRBC Tosetting by Peripheral Blood Lymphocytes of Patients with Hematologic Disorders[a]

| Patient | Disorder | Percent RhMRBC Rosette Forming Lymphocytes | Percent SRBC Rosette Forming Lymphocytes |
|---------|----------|-------------------------------------------|------------------------------------------|
| RS | Mononucleosis[b] | 72 | 74 |
| MS | Mononucleosis[c] | 59 | 64 |
| LM | Chronic lymphocytic leukemia[d] | 81 | 6 |
| VC | Acute lymphocytic leukemia[e] | 93 | 51 |
| AM | Lymphosarcoma cell leukemia[f] | 18 | 15 |

[a] Blood counts performed in conjunction with diagnosis and treatment of these patients were all done by the clinical hematology laboratory of the Massachusetts General Hospital.
[b] Patient RS had typical acute infection mononucleosis with lymphocytosis and atypical lymphocytes (89%). His serum was heterophile antibody positive usually indicating the presence of EBV. We did not attempt to demonstrate viral markers in the lymphocytes of this patient.
[c] Patient MJ also had acute infectious mononucleosis with lymphocytosis but with fewer atypical lymphocytes (13%). His serum was negative for heterophile antibody. Cytomegalovirus (CVM) was isolated from lymphocytes of this patient.
[d] Patient LM with chronic lymphocytic leukemia was not undergoing chemotherapy. Her leudocyte count was 13300 cells/mm$^3$.
[e] Patient VC was in partial remission as a consequence of chemotherapy at the time of this study. His leukocyte count was 11300 cells/mm$^3$.
[f] Patient AM remained refractory to chemotherapy at the time of this study. His leukocyte count was 201500 cells/mm$^3$.

TABLE IV

[$^3$H] Thymidine Uptake Following Incubation with Mitogenic Agents

| Donor | Agent | Day 2 CPM | Day 2 S.I.[b] | Day 4 CPM | Day 4 S.I. | Day 8 CPM | Day 8 S.I. |
|-------|-------|-----------|----------|-----------|------|-----------|------|
| PE | Control | 546 ± 99 | 1.0 | 3714 ± 315 | 1.0 | 3714 ± 315 | 1.0 |
|    | FCS | 1626 ± 135 | 3.0 | 13420 ± 1917 | 3.6 | 87981 ± 22427 | 23.7 |
|    | PWM | 40733 ± 3013 | 74.6 | 107339 ± 5488 | 28.9 | 45699 ± 6681 | 12.3 |
|    | CEM supernatant | 1275 ± 190 | 2.3 | 903 ± 143 | 0.2 | 1189 ± 670 | 0.3 |
|    | UV irradiated CEM supernatant | 1566 ± 373 | 2.9 | 4599 ± 656 | 1.2 | 1559 ± 237 | 0.4 |

| Donor | Agent | Day 5 CPM | Day 5 S.I. | Day 9 CPM | Day 9 S.I. |
|-------|-------|-----------|------|-----------|------|
| MC | Control | 507 ± 76 | 1.0 | 165 ± 30 | 1.0 |
|    | FCS | 10915 ± 3679 | 21.5 | 26110 ± 12318 | 158.2 |
|    | PWM | 39847 ± 3236 | 78.6 | 10080 ± 2551 | 61.1 |
|    | Con A | 28702 ± 9132 | 56.6 | 1858 ± 1164 | 11.3 |

| Donor | Agent | Day 3 CPM | Day 3 S.I. | Day 6 CPM | Day 6 S.I. |
|-------|-------|-----------|------|-----------|------|
| BC | Control | 2103 ± 310 | 1.0 | 3923 ± 76 | 1.0 |
|    | FCS | 3117 ± 427 | 1.5 | 67256 ± 9411 | 17.1 |
|    | PWM | 158818 ± 10288 | 75.5 | 69568 ± 4751 | 17.7 |
|    | LPS | 7647 ± 5703 | 3.6 | 16422 ± 2319 | 4.2 |

[a] All data is reported as counts per minute (CPM) ± standard deviation for five replicate samples.
[b] S.I. is the stimulation index; S,I, = CPM with mitogenic agent/CPM of control cultures.

TABLE V

RhMRBC and SRBC Rosetting by Fractionated Peripheral Blood Lymphocytes of Normal Donors[a]

| Lymphocyte Fraction | Percent RhMRBC Rosette Forming Lymphocytes | Percent SRBC Rosette Forming Lymphocytes | Percent RhMRBC + SRBC Rosette Forming Lymphocytes[b] |
|---------------------|---------------------------------------|-----------------------------------------|------------------------------------------|
| Unfractionated PBL | 58 | 60 | 60 |
| Anti-Ig T + null[c] | 88 | 84 | 88 |
| Anti-Ig B | 80 | 12 | N.D.[d] |
| Nylon Wool T[e] | 91 | 82 | 90 |
| Nylon Wool B + null | 78 | 8 | 76 |
| SRBC-FH T[f,g] | N.D. | N.D. | N.D. |
| SRBC-FH B + null | 78 | 8 | 76 |
| RhMRBC-FH T[g,h] | 84 | 84 | N.D. |

TABLE V-continued

RhMRBC and SRBC Rosetting by Fractionated Peripheral Blood Lymphocytes of Normal Donors[a]

| Lymphocyte Fraction | Percent RhMRBC Rosette Forming Lymphocytes | Percent SRBC Rosette Forming Lymphocytes | Percent RhMRBC + SRBC Rosette Forming Lymphocytes[b] |
|---|---|---|---|
| RhMRBC-FH B + null | 1 | 0 | N.D. |

[a]Cells used in this experiment were from donor GM.
[b]Equal numbers of SRBC and RhMRBC were mixed together for assay as in Table II.
[c]T + null fraction consists of nonbinding cells which were collected from an anti-Ig column (rabbit antihuman F(ab')$_2$ antibody coupled to Sepharose 6B). B cell fraction is that eluted with HGG.
[d]N.D. = Not Done.
[e]T cell fraction is nonadherent population; B + null cell fraction is the adherent population eluted as described.
[f]T cell fraction is SRBC rosetting; B + null is nonrosetting population.
[g]These fractions represent population of cells obtained after two rosetting and separation procedures as described in Methods section.
[h]T cell fraction is RhMRBC rosetting; B + null is nonrosetting population.

TABLE VI

RhMRBC, SRBC and Anti-Ig Bead Rosetting by RhMRBC Rosette Fractionated Peripheral Blood Lymphocytes of Normal Donors[a]

| Lymphocyte Fraction | Percent RhMRBC Rosette Forming Cells | Percent SRBC Rosette Forming Cells | Percent Immunobead Rosette Forming Cells[b] |
|---|---|---|---|
| Unfractionated PBL | 63 | 65 | 20 |
| First[c] T | 80 | 79 | 6 |
| First[c] B + null | 12 | 5 | 42 |
| Second[d] T | 87 | 86 | 3 |
| Second[d] B + null | 3 | 2 | 44 |

[a]Cells used in this experiment were from donor A L.
[b]Denote cells with sIg using Biorad immunobeads.
[c]T cell (rosetting) fraction and B = null fraction (nonrosetting) after a single rosetting.
[d]T cell (rosetting) fraction and B + null fraction (nonrosetting) after a repeat separation procedure as described.

EXAMPLE II

This example illustrates that lymphocyte B cells activated with a polycloral activator can be separated from nonactivated cells.

A population of B plus null lymphocytes was obtained as described in Example I, see Table VI. These cells were exposed to pokeweed mitogen (5 mg/ml).

Activation of the cells was followed for 72 hours by analytical RhMRBC and SRBC rosettes as described in Example I. No increase in SRBC was observed. However, RhMRBC increased as expected. At day 3 the cells were separated by preperative RhMRBC rosetting as described in Example I.

Characteristics of the rosettes and non rosetting cells were determined which are summarized in Table VII.

TABLE VII

Fractionation of Pokeweed Mitogen Stimulated Non-T Cells by Preparative RhMRBC Rosetting

| Marker | RhMRBC Rosetting Fraction | Non-RhMRBC Rosetting Fraction |
|---|---|---|
| RhMRBC Rosettes (%) | 89 | 10 |
| SRBC Rosettes (%) | 1 | 2 |
| $^3$H-Thymidine Uptake (CPM) | 21428 ± 2275 | 580 ± 84 |
| Secreted IgG(pg) | 10 | 10 |
| Secreted IgM (CPM) | 446 ± 27 | 46 ± 15 |
| cell associated | 2280 ± 255 | 433 ± 18 |
| Large Cells (%) | 25 | 0 |
| Small Cells (%) | 75 ± 5.7 | 100 ± 0.3% |
| Complement Receptors (%) | | |
| Total | 30 | 1. |
| Large Cells | 0. | — |
| Small Cells | 39 | 1. |
| Surface Ig(%) | | |
| Total | 12 | 2 |
| Large Cells | 6 | — |
| Small Cells | 23 | 2 |

As shown in Table VII, neither fraction rosetted sheep cells to any significant extent, indicated lact of T cells in the preparation. The rosettes population was about 90% positive for Rhesus monkey rosetting cells were 90% non-rosetting.

$^3$H-thymidine uptake indicates there is substantial DNA synthesis in the rosetting fraction but not the non-rosetting fraction. Tis indicates that cells in the rosetting fraction were proliferating. Rosetting and non-rosetting cells were incubated for 24 hours with $^{14}$C luecine which intrinsically radiolabeled synthesized cell proteins. Radiolabeled IgM was detected in cell supernatants by specific immuno precipitation. As shown in Table VII, a substantial synthesis and secretion of IgM was shown only in the rosetting fraction.

I claim:

1. The process for separating activated animal B lymphocytes that produce immunoglobulin from immunologically inactivate animal cells which comprises:
   (a) exposing animal lymphocyte cells to a stimulation agent selected from the group consisting of a polyclonal activator, an antigen and T cell products induced by an antigen or a polyclonal activator which products normally induce B-cells to produce an antibody;
   (b) incubating said cells exposed to said stimulation agent in order to induce at least some of the B lymophocyte cells of said stimulated cells to form a surface marker that binds with Rhesus monkey erythrocytes;
   (c) contacting said stimulated cells with Rhesus monkey erythrocytes to effect binding thereof with said cells having said surface marker; and
   (d) separating said cells bound to said erythrocytes from cells not bound with said erythrocyte.

2. The process of claim 1 wherein said animal lymphocyte cells are exposed to an antigen.

3. The process of claim 1 wherein said animal lymphocyte cells are exposed to a polyclonal activator.

4. The process of claim 1 which includes the further step of separating T cells from B cells bound with said erythrocyte.

5. The process of claim 1 wherein said animal lymphocyte cells are exposed to said stimulation agent in vivo.

6. The process of claim 1 wherein said animal lymphocyte cells are exposed to said stimulation agent in vitro.

7. The process of claim 1 wherein T cells in said animal lymphocyte cells are separated from said cells prior to exposing said cells to said stimulation agent.

8. The process of any one of claims 1 through 7 wherein said animal is a human.

9. The process of claim 1 wherein the agent is anti-immunoglobulin.

10. The process of claim 1 wherein the agent is an antigen antibody system which leads to formation of surface immunoglobulin on the B lymphocyte cells.

11. The process of claim 1 wherein the stimulation agent comprises T cell products induced by an antigen or a polyclonal activator which products normally induce B cells to produce antibody.

* * * * *